United States Patent
Remberg et al.

(10) Patent No.: US 7,118,770 B2
(45) Date of Patent: Oct. 10, 2006

(54) ARTEMISIA EXTRACT FOR TREATING ALLERGIES

(75) Inventors: Per-Olof Remberg, Sankt (SE); Lars-Olof Björk, Nacka (SE); Thomas Hedner, Gällstad (SE); Olov Sterner, Malmö (SE)

(73) Assignee: Denovastella AB, Sankt IBB (SE)

( * ) Notice: Subject to any disclaimer, the term of this patent is extended or adjusted under 35 U.S.C. 154(b) by 0 days.

(21) Appl. No.: 10/432,375

(22) PCT Filed: Nov. 21, 2001

(86) PCT No.: PCT/SE01/02573

§ 371 (c)(1),
(2), (4) Date: May 21, 2003

(87) PCT Pub. No.: WO02/41909

PCT Pub. Date: May 30, 2002

(65) Prior Publication Data

US 2004/0052875 A1    Mar. 18, 2004

(30) Foreign Application Priority Data

Nov. 22, 2000    (SE) .................................... 0004283

(51) Int. Cl.
*A61K 36/282* (2006.01)
*A61K 36/00* (2006.01)
(52) U.S. Cl. ...................................... 424/740; 424/725
(58) Field of Classification Search ............. 424/195.1, 424/725, 740
See application file for complete search history.

(56) References Cited

U.S. PATENT DOCUMENTS 1,926,929 A    9/1933    Abelmann et al.
6,060,061 A    5/2000    Breton et al.

OTHER PUBLICATIONS

Balachandran et al. Chemical Investigation of Some *Artemisia* Species; Search for Artemisinin or Other Related Sesquiterpene Lactones with a Peroxide Bridge; Indian J. Of Pharm. Sci. (1987) vol. 49, No. 4, pp. 152-154.*
Derwent Abstract, Patent Abstract of Japan, Abstract No. 2000290189, Oct. 17, 2000.
Patent Abstracts of Japan, Abstract No. 10287580, Oct. 27, 1998.

* cited by examiner

*Primary Examiner*—Patricia Leith
(74) *Attorney, Agent, or Firm*—William E. Jackson, Esq.; Stites & Harbison PLLC

(57) ABSTRACT

A method of making a preparation having effect against allergic symptoms, more particularly a preparation which has proved to be effective for therapeutic and prophylactic relief or prevention of symptoms associated eith allergic rhinitis, asthmatic conditions and other allergic conditions, such as allergic conjunctivitis, urticaria, or insect or plant stings, and in which fresh, newly harvested plants of the species *Artemisia* or other davanon containing plants are boiled in water (1), whereby water steam and volatile essential oils are given off, said oils are collected (2), the residue green mass is heated in water to allow for hydrolysis of the chemical components (3) which are extracted with alcohol (4) and are mixed with the previously extracted essential oils. The alcohol extract could be exchanged for an extract of another plant (e.g. thyme or chamomile) containing spasmolytic or antiallergic components. The invention also relates to a preparation made according to the method.

14 Claims, 1 Drawing Sheet

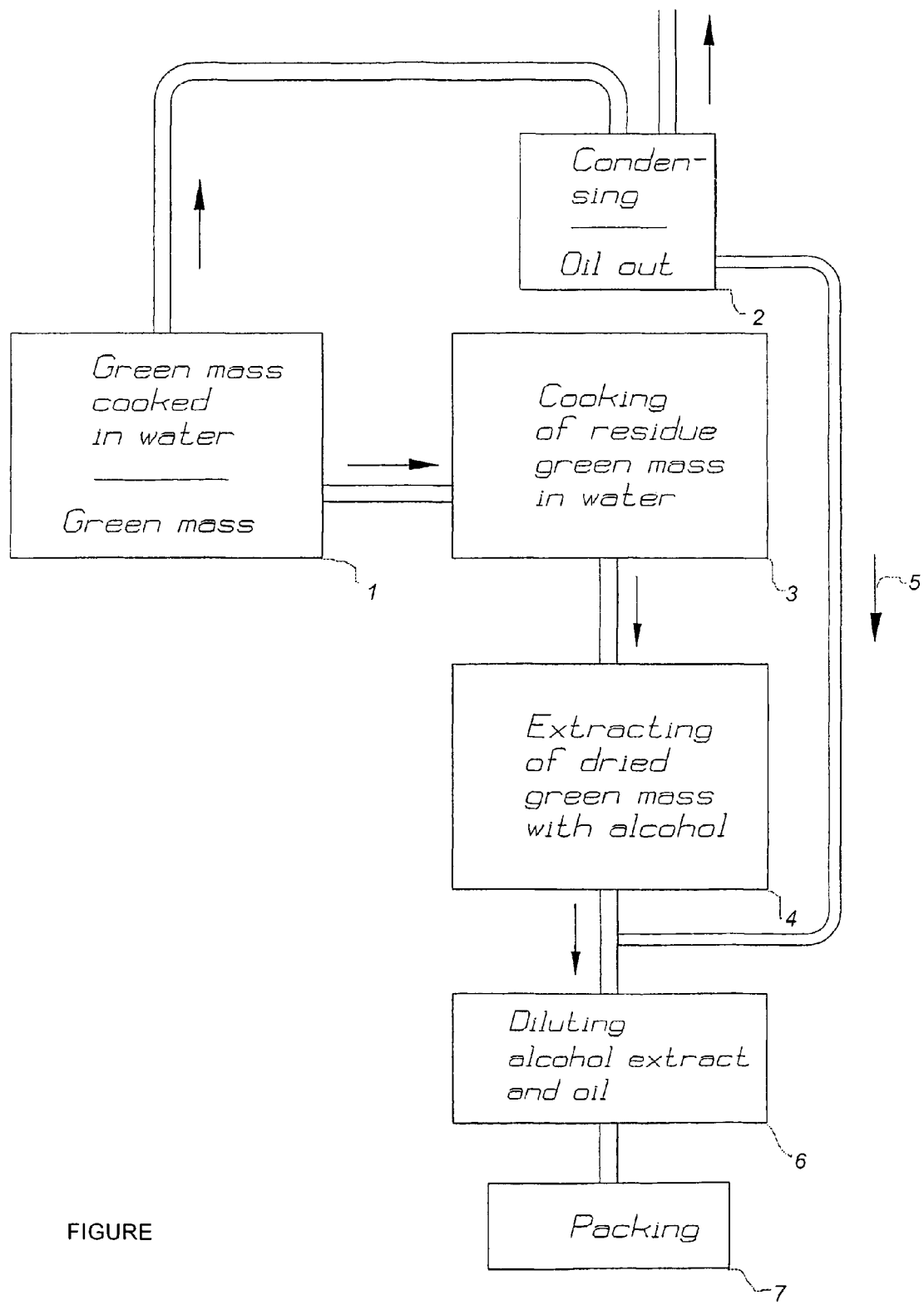
FIGURE

ARTEMISIA EXTRACT FOR TREATING ALLERGIES

The present invention relates to a method for making preparations having effect against allergic symptoms, more particularly a preparation which has proved to be effective for therapeutically and prophylactically relieving discomforts connected to allergic rhinitis and asthmatic affections, for instance exercise induced or airway obstruction asthma bronchiale, allergic conjuctivitis urticaria and other types of allergic symptoms or disorders. The preparation is a nature-cure medicine which can be used for self medication and can be administered as a nasal spray, or by inhalation in airways by spray or powder. The preparation can also be prepared for topical administration in eyes or on skin or on mucous membrane. It is also possible to add the preparation to various kinds of foods. The preparation has been shown to give a good therapeutic as well as prophylactic effect for said allergic conditions.

Surprisingly it has been shown that certain substances which have a good effect against different allergic affections, including asthmatic upper airways conditions, can be extracted from plants. It has also been shown that the preparations made according to the invention have rapid onset and prolonged effect. Importantly, the effect can be obtained already within two minutes. The therapeutic effect remains for a considerable period of time after the preparation has been administered.

The plants which are relevant in this connection are certain species of *Artemisia*, in particular *Artemisia abrotanum* (southernwood) and other davanon containing plants, *A. pallens, A. lerchiana, A. thuscula, A. rehan, A. persica, A. glabella,* and *A. rupestris,* but also *Lantana camara* and *Tanacetum vulgare*. A part of the extract can also be substituted by extracts from other plants having spasmolytic activity, e.g *Thymus vulgaris* or *Chamomilla recutita.*

Certain problems have appeared in the manufacture of the preparation. Previously it has been common procedure that the plant was dried, and that an extract is prepared from the dried plant. This does not, however, work in the present case. It has also been shown that the plant must be relatively young and that the preparation is made from fresh plants which have been harvested (in Scandinavian climate) during May–July. At a later harvest the plant grows woody, it becomes difficult to extract the plant to obtain the desired preparation, and it gives a bitter taste. This depends on the fact that the content of essential oils in the green mass of fresh plants is higher than that of dried plants, and that the composition of different essential oils in the fresh green mass is different from that of more woody plants. During the course of the growth there is a change of the essential oil fraction which is unfavorable for this purpose. While the total content of essential oils is relatively constant, the content of the valuable oil component davanon decreases whereas the content of 1.8-cineol increases. Attempts have been made to use eucalyptus oil as the oil fraction of the preparation, eucapyptus oil contains a high amount of 1.8-cineol which is the main component of the oil from southernwood during late summer. This preparation has been shown to be marginally effective. It can be established that the presence of the oil component davanon, on the contrary, strongly improves the activity of the preparation. While preparations from southernwood having a high content of davanon gives full effect within two minutes, a corresponding product in which the oil has been substituted by eucalyptic oil, exhibits only about 50% of the effect. Tests also have been made in which the essential oil part has completely been substituted by davanon.

It has also been shown that an extract of only the green mass of the plant does not give the desired result, also the extraction and use of only the essential oils of the plant does not give the desired results. On the contrary, if, firstly, the essential oils of the plants are separated from the plant by steam distillation whereupon the remaining green mass is extracted with alcohol, and the essential oils and the alcohol extracts are mixed, an effective product is obtained.

100 g dry plant material of the entire plant southernwood, without the root, contains the following flavonols:
7 mg Casticin
5 mg Centaureidin
5 mg Quercitin 3.4-dimethyl ether
5 mg Quercetin 3.7-dimethyl ether Several variants of the above indicated preparation have been tested and it was shown that the amount of flavonols can vary within certain limits, even if the above mentioned values are considered to give optimum effects:
Casticin 1–8 mg
Centaureidin 1–7 mg
Quercetin 3.4-dimethyl ether 0.5–8 mg
Quercetin 3.7-dimethyl ether 0.5–8 mg It is not clear why a good effect of a preparation of the essential oils added to an alcohol extract of the residue green mass is obtained, but the following are hypotheses:

The plant contains flavonol glycosides and it may be that the flavonol fraction of the plant needs to be deglycosylated in order to become active;

The oil fraction obtained from younger plants, harvested in the beginning of the summer, is more active than oil from plants harvested later;

The preparation should be made from fresh green mass since the oil fraction of the plant contains volatile components which get lost when the plant is dried;

There is a synergistic effect between the oil fraction and the flavonol fraction;

It is possible that the essential oil prepare the mucous membranes so that the flavonols can enter the cells and thereby induce their effect.

Preferred oil contents are between 0.2 ml and 0.0005 ml per 20 ml of the product.

A further problem in producing the preparation is that most of the actual *Artemisia* species, e.g. southernwood, can not be cultivated by seed cultivation, but the cultivation has to be made by cutting breeding. This gives, however, the advantage that the grown material becomes a clone of a so called chemotype, having a defined chemical composition. A special clone has been selected and used in the clinical tests. This clone does not produce thujone when grown under Swedish climate conditions.

In a preliminary clinical experimental study, in which seven test persons were subjected to, among other things, horsehair and cat, allergic symptoms as mucous swelling and running nose were observed. The preparation made according to the above was administered:

1. Before provocation with allergen for instance from dog and cat; no allergic symptoms were observed;
2. After provocation of allergic symptoms with horsehair; the symptoms of rhinitis and running nose disappeared with two minutes;
3. In subjects with exercise induced asthmatic symptoms, induced by for example long distance running; the symptoms disappeared and the test person was free from symptoms within 5–8 minutes;

4. For patients with allergic symptoms from the eyes, so called conjunctivitis, also these symptoms disappeared within the same time frame.
5. In patients with inflammation on mucous membranes, such as sores on the lip or other inflammations such as gingiritis; substantial symptom relief occurred.

In all cases in said preliminary study a full effect was quickly obtained without any remaining symptoms. The only adverse effect that could be noted was a slight smarting pain of short duration in the nose while spraying the preparation.

The most important fields of use for the preparation according to the invention can be considered to be exercise induced asthma, allergic rhinitis, allergic conjuctivitis, and urticaria. For these disorders or diseases the preparation may very well be used for self medication. The preparation can also be used in the therapeutic as well as prophylactic management of the above mentioned different conditions. The preparation has also been demonstrated to have a good effect on insect stings from many different types of insects like mosquitoes, gnats, wasps, bees, horse-flies etc.

The chemical composition of the plant has been documented in various scientific investigations. Thus, the plant contains flavonols, which exhibit a spasmolytic effect in vitro, and terpenes like cineol (antiseptic and mucolytic compound) as well as davanon. The studies mentioned above represent the first tests in which the preparation has been used against allergic symptoms in vivo as well as in local or topical pharmaceutical preparations.

Flavonols represent a group of well defined so called secondary metabolites, which are found in most plants. The flavonols show variations in the number of hydroxyl groups and in the degree of methylation. In the plants, the flavonols present are bound to sugar molecules, but these products are hydrolyzed to liberate the free flavonols during the extraction procedure.

Flavonols from southernwood can induce significant therapeutic effects. Other *Artemisia* species may contain alternative flavonols than those from southernwood. It is, for instance, known that flavonols from onion may inhibit the liberation of histamine, which might accentuate symptoms in a variety of allergic disorders.

Importantly, the flavonol fraction by itself in southernwood extracts does not induce any noticeable therapeutic effect in allergic conditions although such preparations may have a spasmolytic activity. Furthermore, the combination of southernwood oil and directly extracted fresh green mass does not have antiallergic effects either, nor does preparations made from dried green mass and southernwood oil from dried plants elicit therapeutic effects in allergic conditions. Extracts from fresh green mass combined with an oil fraction in which davanon is the main component, such as eucalyptus oil, shows a weak effect, however not to the extent as the therapeutic properties of the combination of alcoholic extract from green mass of southernwood and southernwood oil. The essential oil from *A. thuscula* has been shown to exhibit a spasmolytic effect in the airways of guinea pigs. This effect is dependent on the content of davanon in the preparation.

In the accompanying FIGURE, a flow chart is shown of a procedure to make a preparation from an *Artemisia* species like *A. abrotanum* (southernwood), having effect against allergic symptoms. The process includes seven successive steps schematically represented by boxed or arrows in the FIGURE.

In step (1), fresh southernwood, preferably harvested in the month of June or July (in Scandinavian climate) is boiled in water. Water and certain volatile oils are distilled, as marked with the arrow in the accompanying drawing.

In step (2), water steam and oils are allowed to condense, whereby the essential oils become separated and are collected for later use.

In step (3), the pre-cooked green mass of step (1) is cooked in water for 5–60 minutes. By such cooking the composition is changed chemically, and the flavonol glycosides which are present in the plant are hydrolyzed to free flavonols and sugar.

In step (4), the green mass is dried, and thereafter extracted with alcohol. The free flavonols are dissolved in the alcoholic extract.

In step (5), represented by an arrow from the box representing step (2), essential oils, which were separated and collected in step (2), are admixed into the alcoholic extract from step (4).

In step (6), the mixture of the essential oils from step (2) and the alcoholic extract from step (4) are diluted in water to an alcohol content of about 25%, whereby a final product is obtained. A lower alcohol content reduces the solubility of the oil whereas a higher alcohol content is irritating to the mucosa.

In step (7), the product from step (6) is further processed to provide a suitable preparation for e.g. topical use and then packed in a suitable package, for instance a spray container in order to make it possible to spray the preparation into the nose or the throat, use it in eye drops or apply it topically to the skin, mucous membranes or teeth, or alternatively for use as an additive in food products or other products.

In the following non-limiting examples provided for exemplary purposes only, which in no way limit the scope of the present invention, three different extracts were used: FI, a concentrated extract containing 8 mg Casticin, 7 mg centaureidin, 8 mg quercetin 3.4-dimetyl-ether and 8 mg quercetin 3.7-dimethyl-ether; extract F2, which is the extract FI diluted 1:4 with 24% ethanol; extract F3, which is the extract FI diluted 1:10 with 24% ethanol.

EXAMPLES

Example 1

Woman, 45 years old, nurse. The patient suffers from bronchial asthma under physical effort (jogging). The patient used a preparation, extract F1 according to the present invention (instead of Terbutalin (Bricanyl, Draco). The preparation contained 0.1 ml essential oil per 20 ml alcohol. Full effect was reached within 2 minutes.

Example 2

The same patient used a preparation, extract F1 containing 0.2 ml essential oil per 20 ml alcohol. Full effect was obtained within 2 minutes, only slightly or not better than in example 1 at different tests.

Example 3

The same patient used a preparation, extract F1 containing 0.05 ml essential oil per 20 ml alcohol. There was obtained somewhat lower effect than in examples 1 and 2

Example 4

The same patient used a preparation, extract F2 containing 0.05 ml essential oil per 20 ml alcohol. There was obtained somewhat lower effect than in examples 1 and 2.

Example 5

A male, 48 years old, a district medical officer, allergic to cat, dog, pollen and horse, suffers from bronchial asthma under physical effort (jogging). Provocation by allergy agent followed by use of allergic spray according to the invention after asthmatic attack. The spray contained 0.1 ml essential oil per 20 ml alcohol, extract F1. The patient became free of symptoms within 2 minutes.

Example 6

Same patient as in example 5 was treated with a spray according to the invention containing 0.1 ml essential oil per 20 ml alcohol of extract F2. The symptoms were reduced but the patient was not fully cures within 2 minutes.

Example 7

Same patient as in examples 5 and 6 was treated with a spray according to the invention containing 0.1 ml essential oil per 20 ml alcohol of extract F3. Certain reduction of the pain was obtained within 5 minutes but the patient was not fully cured.

Example 8

The same preparation as in example 5 was taken for preventive purpose 5 minutes by the same person as in examples 5–7 before provocation by allergens. Provocation was made by horsehair and by cat. No symptoms occurred.

Example 9

A male farmer, 54 years old suffers from allergic rhinitis and itching eyes when exposed to hay and air from swine stable. He has taken the preparation according to the present invention instead of terbutalin. A preparation was taken, for preventive purposes, containing 0.05 ml of the essential oil per 20 ml of the alcohol extract of F1. No problems occurred within 2 hours.

Example 10

The same patient administered a preparation containing 0.05 ml of the essential oil according to the invention per 20 ml alcohol extract of F3. Slight problems occurred within 5 minutes.

The above examples thus show that the highest amount of oil should not be higher than 0.2 ml per 20 ml of the product, and that the lowest value should not be less than 0.0005 ml per 20 ml of the product.

As also indicated above the lowest and the highest amount of flavonols ought to be for Casticin 1–8 mg
for Centaureidin 1–7 mg
for Quercetin 3.4-dimethyl ether 0.5–8 mg
for Quercetin 3.7-dimethyl ether 0.5–8 mg Flowchart:
1. Fresh biomass boiled in water
2. Condensation. Essential oils collected, water phase discarded.
3. Boiling of residue green mass. Drying.
4. Extraction of dry biomass with alcohol.
6. Dilution of oil/extract mixture.
7. Packing.

The invention claimed is:

1. A method of obtaining extract from *Artemisia* plants, said method comprising the steps of:
   (i) distilling fresh, newly harvested plants selected from the group consisting of *Artemisia abrotanum, Artemisia pallens, Artemisia lerchinia, Artemisia thuscula, Artemisia rehan, Artemisia persica, Artemisia glabella, Artemisia rupestris, Lantana camara* and *Tanacetum vulgare* by boiling to obtain an essential oil comprising davanon and 1,8-cineol and a remaining residual green mass of plant material;
   (ii) heating the residual green mass of step (i) in water to hydrolyze the flavonol glycosides therein to free flavonols and sugar;
   (iii) drying the residual green mass and extracting the green mass with alcohol to obtain an alcoholic extract of said residual green mass containing free flavonols; and
   (iv) combining the alcoholic extract of residual green mass containing free flavonols of step (iii) with the essential oil comprising davanon and 1,8-cineol obtained in step (i) to obtain the extract.

2. The method according to claim 1, wherein said essential oil in step (i) is obtained from the top of the water after being separated from said residual green mass of plant material.

3. The method according to claim 2, wherein said heating in step (ii) is 5 to 60 minutes.

4. The method according to claim 2, wherein said extraction with alcohol in step (iii) is made so that non-volatile substances are extracted from said residual green mass.

5. The method according to claim 1, wherein said heating in step (ii) is 5 to 60 minutes.

6. The method according to claim 1, wherein said extraction with alcohol in step (iii) is made so that non-volatile substances are extracted from said residual green mass.

7. The method according to claim 6, wherein said extract in step (iv) is further diluted to an alcohol concentration of about 0–40%.

8. The method according to claim 7, wherein said extract in step (iv) is further diluted to an alcohol concentration of 25%.

9. The method according to claim 1, wherein said obtained extract in step (iv) is processed into and packed as a nasal or throat spray or powder, or as a topical composition for use in eyes or on skin or on mucous membranes or teeth.

10. The extract obtained from step (iv) of claim 1.

11. The product of claim 10, wherein said product is obtained from *Artemisia abrotanum* L.

12. The method of claim 1 wherein said plant is *A. abrotanum*.

13. A method of treating disorders selected from the group consisting of allergic rhinitis, asthma, insect stings and plant allergies by administering an effective amount of the extract of claim 10.

14. The method of treatment of claim 13, wherein the extract is obtained from *Artemisia abrotanum* L.

* * * * *